United States Patent
Sherman

(10) Patent No.: US 9,072,516 B2
(45) Date of Patent: Jul. 7, 2015

(54) METHOD AND APPARATUS TO REGULATE A TISSUE TEMPERATURE

(71) Applicant: Medtronic, Inc., Minneapolis, MN (US)

(72) Inventor: Marshall Sherman, Cardiff by the Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 0 days.

(21) Appl. No.: 14/320,677

(22) Filed: Jul. 1, 2014

(65) Prior Publication Data
US 2015/0018708 A1 Jan. 15, 2015

Related U.S. Application Data

(62) Division of application No. 12/770,797, filed on Apr. 30, 2010, now Pat. No. 8,834,388.

(51) Int. Cl.
| | |
|---|---|
| *A61B 5/00* | (2006.01) |
| *A61B 18/08* | (2006.01) |
| *A61B 18/14* | (2006.01) |
| *A61B 5/01* | (2006.01) |
| *A61B 17/00* | (2006.01) |
| *A61B 18/00* | (2006.01) |

(52) U.S. Cl.
CPC ........... *A61B 18/082* (2013.01); *A61B 18/1492* (2013.01); *A61B 2017/00092* (2013.01); *A61B 2017/00101* (2013.01); *A61B 2018/00357* (2013.01); *A61B 2018/00577* (2013.01); *A61B 2018/00702* (2013.01); *A61B 2018/00791* (2013.01); *A61B 2018/00797* (2013.01); *A61B 2018/00821* (2013.01); *A61B 5/01* (2013.01); *A61B 2018/00714* (2013.01)

(58) Field of Classification Search
CPC ................... A61B 18/00; A61B 2018/00571; A61B 2018/00791; A61B 2018/00797; A61B 2018/00821; A61B 18/1492; A61B 5/01; A61B 2017/00092; A61B 2017/00084; A61B 2017/00101
USPC ................... 600/549; 374/100; 702/130, 131; 606/27, 32, 39, 40
See application file for complete search history.

(56) References Cited

U.S. PATENT DOCUMENTS

| | | | |
|---|---|---|---|
| 3,273,395 A * | 9/1966 | Schwarz | ............ 374/133 |
| 4,411,266 A | 10/1983 | Cosman | |
| 4,945,912 A | 8/1990 | Langberg | |
| 4,955,377 A | 9/1990 | Lennox et al. | |
| 4,966,597 A | 10/1990 | Cosman | |
| 5,122,137 A | 6/1992 | Lennox | |
| 5,230,349 A | 7/1993 | Langberg | |
| 5,456,682 A | 10/1995 | Edwards et al. | |
| 5,500,012 A | 3/1996 | Brucker et al. | |
| 5,688,267 A | 11/1997 | Panescu et al. | |
| 5,711,607 A * | 1/1998 | Bernstein | ............ 374/179 |
| 5,735,846 A | 4/1998 | Panescue et al. | |
| 5,810,802 A | 9/1998 | Panescu et al. | |
| 5,849,028 A | 12/1998 | Chen | |

(Continued)

FOREIGN PATENT DOCUMENTS

EP 2338431 A1 6/2011

Primary Examiner — Max Hindenburg
Assistant Examiner — Jonathan M Foreman

(57) ABSTRACT

A system and method are described for sensing the orientation of a catheter relative to a tissue and regulating the application of power to maintain the tissue at a pre-determined temperature.

11 Claims, 10 Drawing Sheets

(56) References Cited

U.S. PATENT DOCUMENTS

| | | | |
|---|---|---|---|
| 6,049,737 A | 4/2000 | Simpson et al. | |
| 6,162,184 A | 12/2000 | Swanson et al. | |
| 6,440,129 B1 * | 8/2002 | Simpson | 606/42 |
| 2002/0022834 A1 | 2/2002 | Simpson et al. | |
| 2008/0161797 A1 | 7/2008 | Wang | |
| 2010/0057072 A1 | 3/2010 | Roman et al. | |

* cited by examiner

METHOD AND APPARATUS TO REGULATE A TISSUE TEMPERATURE

FIELD OF THE INVENTION

The disclosure relates generally to ablation of tissue with a medical device.

BACKGROUND OF THE INVENTION

Tissue ablation for the treatment of cardiac arrhythmias may use various sources or heat or cold to modify or prevent conduction within the tissue of the heart with a therapeutically beneficial aim of eliminating the cardiac arrhythmia. Cosman in U.S. Pat. No. 4,411,266 describes a radio frequency lesion electrode design with a thermocouple temperature sensor in its distal uninsulated tip. The instrument was described as a common instrument for neurosurgery to destroy tissue by heat. Because temperature is the basic lesioning or destruction parameter, temperature control or monitoring of the electrode's tip was an essential means for carefully grading the degree or destruction and quantifying the lesion size. A rapid and faithful readout of tissue temperature was often critical to safety and successful results. Thermistor sensors posed a limitation on the outer diameter shaft size of the catheter. Thermocouple sensors did not have the same limitation but presented difficult technical problems in fabrication and suitability in accuracy and speed of thermometric response for very small gauge radio frequency lesion electrodes. A temperature sensor not at the extreme tip end of the electrode produces various sources of inaccuracies. Because the sensor is placed internally in the tip, it senses only the average tissue temperature around the tip which may be significantly below that at the very tip. Such a situation can produce dangerous inaccuracies in a critical procedure. There is a temperature gradient due to the finite mass and heat conduction effects. Thus, the sensor, when not exactly at the surface of the end, will never be at the temperature of the hottest, most critical region near the very tip of the electrode. Langberg in U.S. Pat. No. 4,945,912 describes a catheter for ablating cardiac tissue with means to control the RF power applied to tissue surrounding the catheter tip. Lennox et al in U.S. Pat. No. 4,955,377 describe a device and method for heating tissue, the device having a catheter shaft for insertion into a patient's body, a thermistor sensor to control the application of the current and a carefully controlled therapy can be conducted at a constant temperature.

Cosman in U.S. Pat. No. 4,966,597 describes a device with a faithful and rapid temperature reading in the tissue. Because the electrical junction is exactly at the surface of the electrical surface means no thermal mass effects at the tip and the temperature is precisely the temperature of the adjacent tissue outside of the electrode. Lennox in U.S. Pat. No. 5,122,137 describes a catheter with a temperature sensor carried by and in a thermally conductive relationship with a thermally conductive electrode. The temperature sensor senses the temperature of the electrode, and thereby indirectly senses the temperature of tissue in contact with the electrode. The sensor is connected by a feedback line to a control circuit that automatically modulates RF power applied to the electrode.

Langberg, in U.S. Pat. No. 5,230,349 describes the temperature boundary between viable and non-viable tissue as approximately 48 degrees Celsius (C.). Tissue heated to a temperature above 48 C is non viable. The objective of ablation is to elevate the basal tissue temperature, generally at 37 C, fairly uniformly to the ablation temperature above 48 C, keeping, however, the hottest tissue temperature below 100 C. At approximately 100 C, charring and tissue desiccation take place which seriously modifies the electrical conductivity of blood and tissue, and causes an increase in the overall electrical impedance of the electrical heating circuit and a drop in the power delivery to the tissue. Charring is particularly troublesome at the surface of the catheter electrode since the catheter must be removed and cleaned before the procedure can continue. The active electrode temperature is the result of the balance between conductive heating and convective cooling from the blood.

Edwards et al in U.S. Pat. No. 5,456,682 describe an ablation electrode with a temperature sensing element located on the energy emitting body of the ablation electrode. The temperature sensing element senses the temperature of the tissue being ablated by the electrode. The electrode includes a thermal insulating element located between the energy emitting body and the temperature sensing element. At least one, and preferably all, the temperature sensing elements are thermally insulated. The thermally insulated temperature sensing element measures true tissue temperature, without being affected by the surrounding thermal mass of the electrode.

Brucker et al in U.S. Pat. No. 5,500,012 describe an ablation system for treatment of tachyarrhythmia and identify several problems of the ablation of myocardial tissue as including blood coagulated onto the electrodes during ablation and sometimes difficult to know whether the tissue is being destroyed or whether the energy is being diverted to the catheter or the blood.

Panescu et al in U.S. Pat. No. 5,688,267 describe systems and methods including multiple temperature sensing elements. One element senses tissue temperature. A second element senses electrode temperature. The systems and methods control the supply of ablation energy to the electrode based, at least in part, upon the multiple temperatures sensed by the different temperature sensing elements.

Panescu et al in U.S. Pat. No. 5,735,846 describe systems and method for ablating body tissue using an electrode for contacting tissue at a tissue-electrode interface to transmit ablation energy at a determinable power level. The systems and methods employ a processing element to derive a prediction of the maximum tissue temperature condition occurring beneath the tissue-electrode interface. In one implementation, the processing element controls the power level of ablation energy transmitted by the electrode based, at least in par4t, upon the maximum tissue temperature prediction. In another preferred embodiment, the processing element samples the power level at which the electrode transmits ablation energy, the temperature of the electrode, and the rate at which heart is removed from the electrode to derive the maximum tissue temperature.

Chen in U.S. Pat. No. 5,849,028 describes an electrophysiology catheter suitable for radiofrequency ablation of cardiac tissue with multiple long electrodes and multiple temperature sensors in the proximity of the tissue contact sites and further comprising a close-loop temperature control mechanism for each electrode with at least a temperature sensor on an adjacent tiny ring. The securing point of the temperature sensor on the electrode is usually on the opposite side of the tissue contact point to avoid temperature surge when the RF energy is suddenly delivered. And the measured temperature from said sensor does not reflect the true real-time temperature at the tissue contact point for temperature control purpose. Chen describes as useless when the measured temperature does not reflect the true temperature. Chen provides an ablation catheter having a temperature sensor secured adjacent to an electrode, while not in contact with any electrode, to independently and accurately control the energy delivery to each electrode; wherein the temperature sensor is secured to the proximity of the tissue contact site.

Simpson et al in U.S. Pat. No. 6,049,737 describe a catheter having a plurality of electrodes arranged in a linear array, temperature sensors located at the electrodes and each shares a common lead with the power circuitry. The temperature sensor signal is received by a power control system during the off-period of the duty cycle of the particular electrode. In the case where a catheter has a band electrode, such as for the treatment of atrial fibrillation by the ablation of tissue, a single temperature sensor mounted to the band may not provide the temperature of the tissue contacting the band electrode. Typically, the side of the band which is in direct contact with the tissue becomes significantly hotter than the rest of the band electrode that is cooled by the blood flow. Thus, the temperature reading can be dramatically influenced by the rotational orientation of the catheter during RF ablation. If the band is oriented so that the single temperature sensor is not in contact with the tissue during the application of ablation energy, not only would there be a time lag in the sensor reaching the tissue temperature, but due to the effect of the cooling blood flow, the sensor reading may never approach the actual tissue temperature.

To overcome the effect that the rotation orientation of the band electrode has on temperature sensing, two thermocouples, positioned at different locations of the band electrode, may be used. A theory is that having a sensor in contact with tissue is more likely. While attachment of multiple temperature sensors to the band electrode can result in a higher probability of sensing the actual tissue interface temperature, this also increases the number of wires occupying space within the catheter. As is well appreciated by those skilled in the art, an increase in the number of internal wires could mean an undesirable increase in catheter diameter to accommodate those wires. Conventional types of thermocouples each require a thermocouple wire pair. Two thermocouples at each band electrode would result in four wires per band electrode so that the use of multiple temperature sensors may not be practical, particularly where the catheter carries multiple band electrodes that require temperature monitoring.

The larger the catheter, the more traumatic it is to the patient. Also, the more difficult it may be to negotiate the patient's vessels to position the catheter at the desired location in the heart. It is desirable to provide a catheter with as small a diameter as possible. A limiting factor in reducing the size of the catheter is the amount of devices and leads that must be carried inside the catheter. In the case of a catheter having ten band electrodes with two thermocouple temperature sensors at each electrode, a total of fifty wires would be necessary; one power wire for each electrode and two wires for each thermocouple. The size of fifty wires inside a catheter can be significant, causing an increased diameter of the catheter. Yet it is desirable to retain the electrodes and the associated temperature sensors so that more precise control over the energy applied to the biological tissue can be effected. Thus, it would be desirable to reduce the number of wires within a catheter, yet retain the same functionality.

As designs for ablation catheters incorporate a significant number of electrodes and shapes, it has become important to limit the number of wires that need to be threaded through the catheter and especially through the proximal band electrodes on the catheter. Further, by limiting the number of thermocouples that need to be placed in each electrode, the number of wires that need to be threaded can be achieved. The physician user often finds it difficult to manipulate the ablation catheter to the precise location to achieve the desired therapeutic effect. It is, therefore, desired that an ablation system automatically adapt to any catheter orientation and not require the user to rotate the catheter to a specific orientation.

The invention fulfills the needs described above and others.

SUMMARY

The temperature measured from inside an electrode of a catheter used for RF ablation of a tissue in a patient's heart can be indicative of the temperature of the blood or the temperature of the tissue that is in contact with the electrode, depending on the orientation of the catheter. This disclosure describes techniques for measuring the temperature from two locations inside a catheter, classifying the orientation of a catheter based on the temperature measurements and regulating a power applied to a tissue based on the temperature measurements.

In one example, this disclosure is directed to a system for determining a tissue temperature comprising two thermocouples spaced circumferentially apart in a catheter, an external control unit electrically coupled to the thermocouples and to the catheter, the external control unit applies an energy through the catheter, the external control unit measures a voltage from each thermocouple and the external control unit calculates a tissue temperature based on the thermocouple voltages. In a further example, the external control unit classifies a catheter orientation as one of: neither thermocouple touches the tissue, only one thermocouple touches the tissue and both thermocouples touch the tissue, based on the thermocouple temperatures.

In a further example, the external control unit calculates a compensation temperature and a regulation temperature. The external control unit regulates the power to the tissue based on the regulation temperature.

In another example with multiple electrodes on the catheter and two thermocouples spaced circumferentially apart in the catheter as described above, a nearby electrode needs only one longitudinally aligned thermocouple to regulate the power to the tissue through the nearby electrode.

This summary is intended to provide an overview of the subject matter described in this disclosure. It is not intended to provide an exclusive or exhaustive explanation of the techniques as described in detail within the accompanying drawings and description, below. Other features, objects, and advantages will be apparent from the description and drawings, and from the statements provided below.

DETAILED DESCRIPTION OF THE ILLUSTRATED EMBODIMENTS

Figure 1:
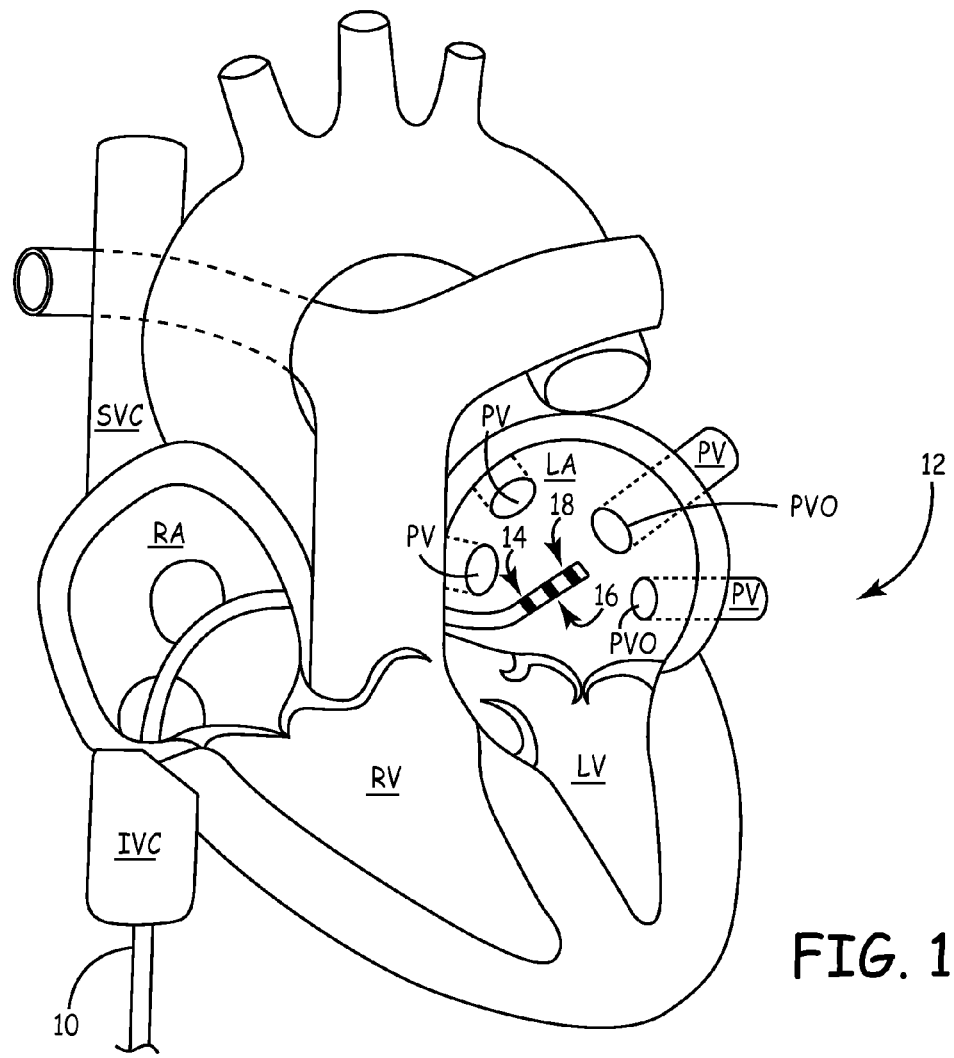
FIG. 1 is a schematic illustration of a catheter in a heart.

With reference to the FIG. 1, the present invention relates to the use of catheter 10 within a patient. The illustrated example is in a patient's heart 12 but could apply to other organs of the body, as well. The example illustrated in FIG. 1 shows catheter 10 placed through the patient's venous system but catheter 10 could be placed in other vessels or be placed in an extravascular space. Catheter 10 has electrodes 14, 16, 18 for contact with tissue in heart 12. Electrodes 14, 16, 18 may be used for diagnostic and/or therapeutic purposes. The number of electrodes can be any number from one or greater and the number is not to be limited by the illustrated example.

Various anatomical portions of the heart are identified by abbreviated callouts and are supplied to aid in understanding general anatomic locations. These include the superior vena cava (SVC), inferior vena cava (IVC), right atrium (RA), right ventricle (RV), left ventricle (LV), left atrium (LA) and the four pulmonary veins (PV). Two of the pulmonary vein ostia (PVO) are denoted.

Figure 2:
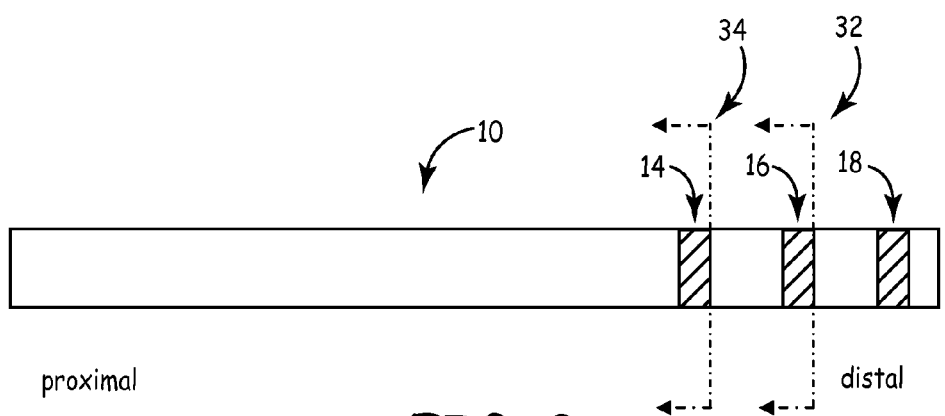
FIG. 2 is a schematic illustration of a catheter with three electrodes and two section lines.

FIG. 2 is a schematic of catheter 10 with electrodes 14, 16, 18 at the distal end of catheter 10. Catheter 10 is displayed in FIG. 1 in the inferior vena cava, through the right atrium and the distal portion in the left atrium of heart 12. Catheter 10 may be lodged, pressed or wedged against the tissue of heart 12 for diagnostic and/or therapeutic intentions. Applying electrical power of sufficient magnitude to one or more of electrodes 14, 16, 18 may heat the heart tissue and result in damage to the tissue. Such damage may be therapeutically useful for the treatment of cardiac arrhythmias. Ablation is a medical procedure that makes use of various techniques to damage tissue so as to prevent the propagation of cardiac depolarizations in specific areas of a heart to prevent further arrhythmic occurrence.

Figure 3:
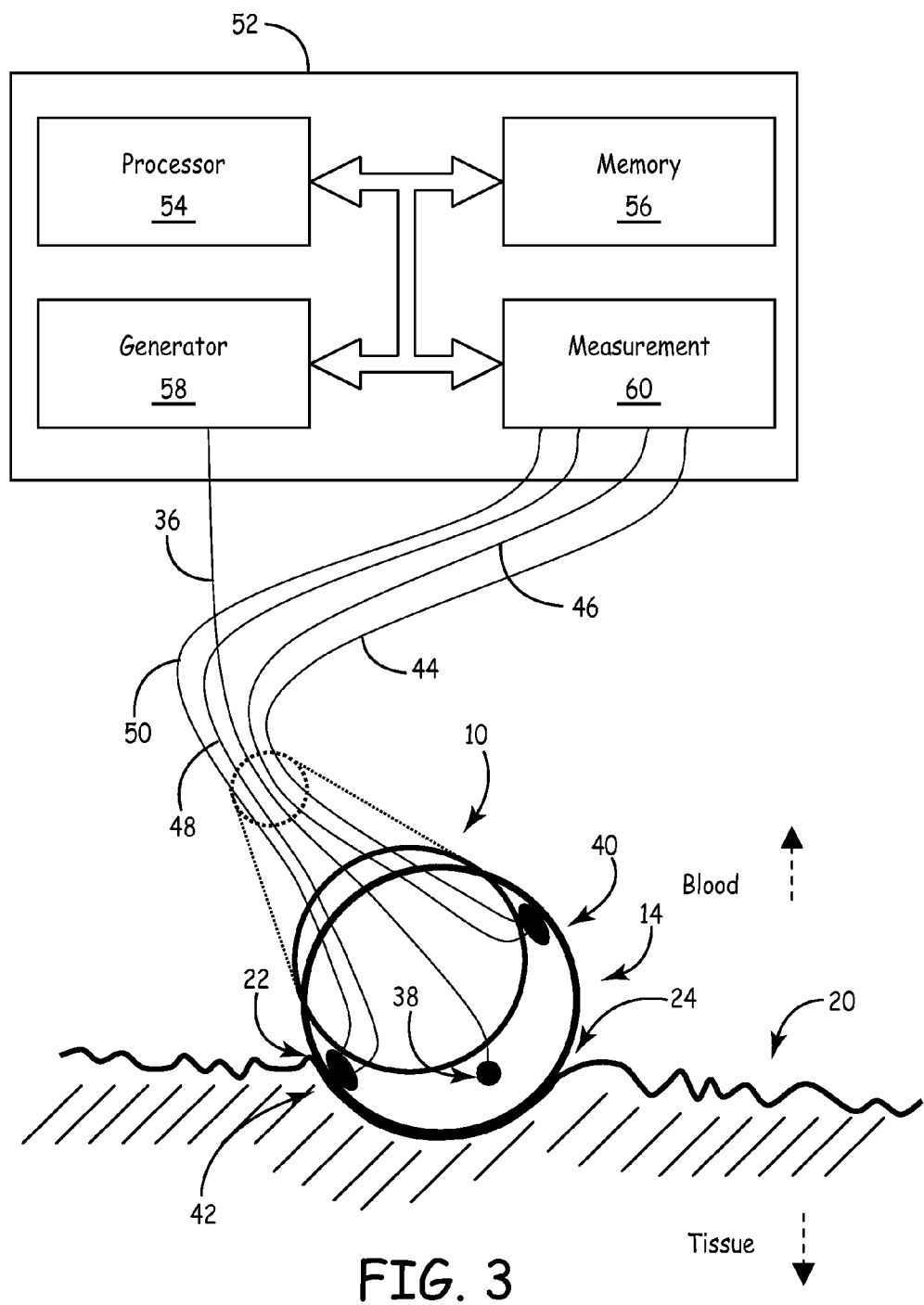
FIG. 3 is a perspective diagram of an electrode on a catheter and a block diagram of an external control unit.

FIG. 3 illustrates a perspective view of catheter 10 viewed from section line 34 (shown in FIG. 2) of electrode 14 towards the proximal end of catheter 10. Two locations 22, 24 are denoted at the junctions of the interface between first tissue 20 and electrode 14. In a beating heart, the temperature at locations 22, 24 are the same, about 37 degrees Celsius, the normal human core body temperature. Electrode 14 is bathed in blood from location 22 clockwise to location 24. Electrode 14 is in contact with first tissue 20 from location 24 clockwise to location 22. With the application of electrical power to electrode 14, power is absorbed by first tissue 20 and the blood. The flow of blood past electrode 14 serves to maintain the blood bathed portion of electrode 14 at or near 37 degrees Celsius while the tissue covered portion of electrode 14 may have a more profound rise in response to the applied power. The effect of heating on the blood is minimal due to the continuous blood flow. With a relatively large volume of blood in the body, the continuous flow of blood over the electrode and the relatively large amount of the tissue in the body that acts as a heat sink to the blood, the blood bathed portion of the electrode remains close to the normal core temperature of the patient and the downstream blood temperature rise negligible. On the other hand, the tissue covered portion of electrode 14 will increase in temperature due to the lack of a circulating coolant. If electrode 14 is thermally conductive, little temperature difference will occur between the blood bathed portion and the tissue covered portion. However, if electrode 14 is a poor thermal conductor, a temperature difference will be noted between the blood bathed portion and the tissue covered portion. If electrode 14 is composed of gold a temperature range of 5 degrees Celsius might be observed while an electrode of platinum might result in a temperature range of 20 degrees Celsius. Thus, the site of a temperature measurement within electrode 14, while electrode 14 is being used to apply power to first tissue 20, can affect the difference between the measured temperature and the actual temperature of first tissue 20. If the site of the temperature measurement corresponds to a portion of electrode 14 which is bathed with blood, the temperature measurement will be consistent with the temperature of the blood and not first tissue 20. If the site of temperature measurement corresponds to a portion of electrode 14 which is in contact with first tissue 20, the temperature measurement will be higher and more closely reflect the actual temperature of first tissue 20.

A perspective view of catheter 10 from section line 34 is shown in FIG. 3. Electrode 14, the most proximal electrode on catheter 10 is illustrated in contact with first tissue 20. Wire connections from the inside of electrode 14 are shown for measuring temperature and applying power to electrode 14. First temperature sensor 40 and second temperature sensor 42 are disposed circumferentially around the interior of electrode 14, the two sensors are placed diametrically apart. Power connection 38 is used to supply power to first tissue 20 through wire 36 and electrode 14. Each of the temperature sensors 40, 42 has two sensor wires 44, 46, 48, 50, respectively, for sensing temperature of first temperature sensor 40 and second temperature sensor 42. The temperature sensors illustrated in FIG. 3 are consistent with thermocouples but could be other types of temperature sensors that could be located on the interior of electrode 14. Thermocouples produce a voltage that is related to their temperature. Thermocouples employ a junction of dissimilar metals and are used widely in applications such as for the control of valves in gas appliances such as heaters. Catheter 10 is navigable within the body for accessing the heart 12 and specifically first tissue 20; catheter 10 is shown as an elongated tube for purposes of illustration. Catheter 10 may include a handle, various pull/push wires and other mechanisms for manipulating the shape of the catheter and an electrical connector for electrically coupling to external equipment. FIG. 3 and other illustrations are illustrative only and should not be interpreted to limit the interpretation of various embodiments of the invention.

External control unit 52 includes processor 54, memory module 56, generator module 58 and measurement module 60. Although the four modules are represented as incorporated within external control unit 52, each of the modules could be constructed as an independent unit or combinations of the four modules could be constructed as separate units. The four modules are shown in external control unit 52 for purposes of illustration. Generator module 58 is connected to electrode 14 at power connection 38 through power conductor 36. First temperature sensor 40 is connected to measurement module 60 through sensor wires 44, 46. Similarly, second temperature sensor 42 is connected to measurement module 60 through sensor wires 48, 50. Measurement module 60 incorporates voltage measurement to measure the voltages of first and second temperature sensors 40, 42.

Figure 4:
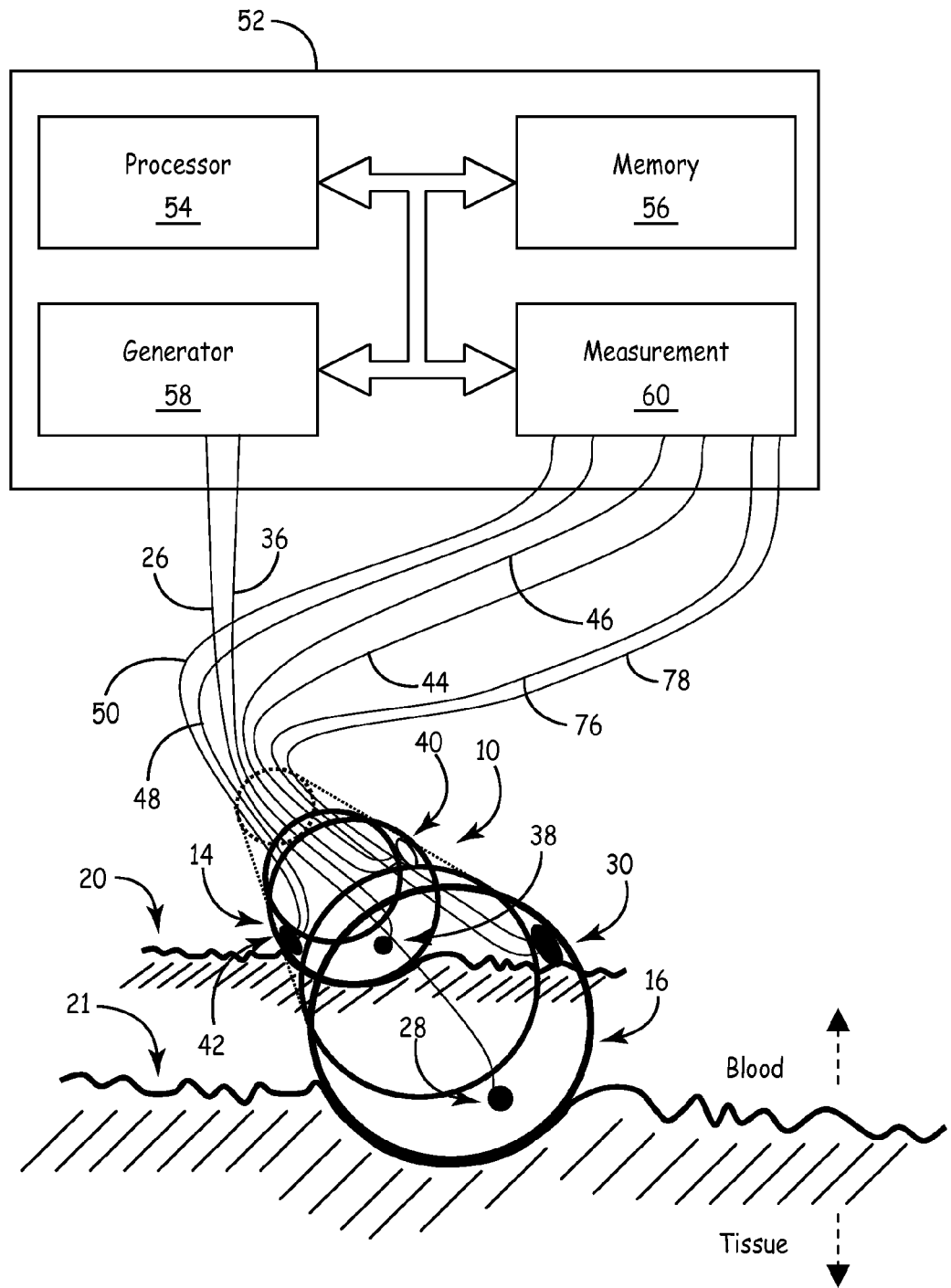
FIG. 4 is a perspective diagram of two electrodes on a catheter and a block diagram of an external control unit.

FIG. 4 is a conceptual illustration of electrodes 14, 16 of catheter 10 relative to first tissue 20 and second tissue 21 viewed from section line 32. First tissue 20 and second tissue 21 are shown in a conceptual perspective view; first and second tissues 20, 21 form a mildly deformable plane. Tissue 20, 21 may deform slightly as catheter 10 applies radial pressure to tissue 20, 21. First temperature sensor 40 and third temperature sensor 30 in electrodes 14, 16, respectively, are spaced longitudinally apart as electrodes 14, 16 are spaced apart. First and third temperature sensors 40, 30 are in longitudinal alignment. If catheter 10 were rotationally oriented, first and third temperature sensors 40, 30 would both be in contact with respective first and second tissues 20, 21 or both would be in contact with the blood. FIG. 4 illustrates an orientation of catheter 10 where first and third temperature sensors 40, 30 are in contact with the blood and are not in contact with first and second tissues 20, 21; second temperature sensor 42 is not in contact with the blood and is in contact with first tissue 20. The location of third temperature sensor 30 with respect to second tissue 21 can be inferred from the measurements of temperature sensors 40, 42. By inferring the location of temperature sensor 30 only one temperature sensor is needed within electrode 16 rather than two sensors as utilized in electrode 14, for the determination of the temperature of second tissue 21 and the regulation of power to electrode 16 to achieve a target temperature of second tissue 21 (described below). The use of a single temperature sensor rather than two temperature sensors within electrode 16 allows manufacturing catheter 10 with a lesser number of conductors and a lesser number of sensors to determine the catheter orientation and regulate power to tissue 20, 21 (described in further detail below). Inference of the position of other nearby electrodes has corresponding advantages with regards to the reduction of the number of conductors and the number of temperature sensors required for manufacture of catheter 10.

Figure 5:
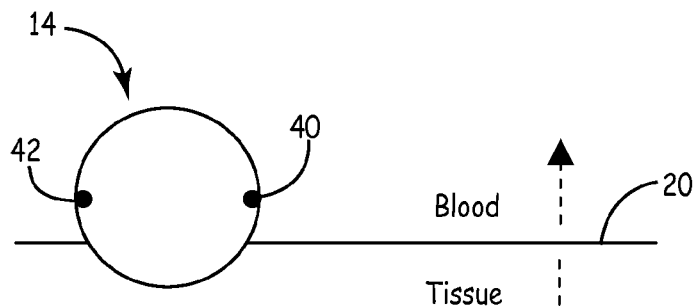
FIG. 5 is a conceptual diagram of a tissue and an electrode with two temperature sensors. The electrode is oriented so neither sensor touches the tissue.
Figure 6:
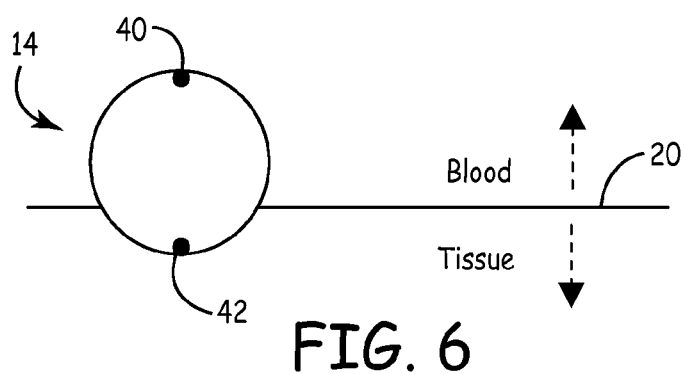
FIG. 6 is a conceptual diagram of a tissue and an electrode with two temperature sensors. The electrode is oriented so one of the sensors touches the tissue.

In FIG. 5, catheter 10 is oriented so first and second temperature sensors 40, 42 are in contact with the blood and not in contact with first tissue 20. When power is applied to first tissue 20 through electrode 14, first and second temperature sensors 40, 42 will essentially remain at the temperature of the blood and will increase little. In FIG. 6 first temperature sensor 40 is bathed in the blood; second temperature sensor 42 is not bathed in the blood and is in contact with first tissue 20. The temperature of second temperature sensor 42 will differ in the two illustrated examples of FIG. 5, 6. In FIG. 5, electrode 14 is oriented so second temperature sensor 42 is located in a portion of electrode 14 that is bathed with the blood whereas in FIG. 6, electrode 14 is oriented so second temperature sensor 42 is in a portion of electrode 14 that is in contact with first tissue 20. With the application of power to first tissue 20 through electrode 14, second temperature sensor 42 will essentially reflect the temperature of the blood in the example illustrated in FIG. 5 and will reflect an increased temperature of first tissue 20 in the example illustrated in FIG. 6. By applying a power to electrode 14, measuring the temperature at first and second temperature sensors 40, 42 and comparing the two temperatures, the external control unit may determine the orientation of first and second temperature sensors 40, 42 and, therefore, the orientation of electrode 14 and catheter 10 with respect to first tissue 20. If the temperatures of first and second temperature sensors 40, 42 remain essentially at the temperature measured before the application of power from external control unit 52, then both temperature sensors 40, 42 are in the blood as illustrated in FIG. 5. However, if only one temperature sensor remains essentially at the temperature measured prior to the application of power from external control unit 52, then one temperature sensor is bathed by the blood and one temperature sensor is in contact with first tissue 20 as illustrated in FIG. 6. The temperature sensor with the higher temperature is the temperature sensor that is in contact with first tissue 20. If neither first nor second temperature sensors 40, 42 essentially remain at the temperature that is measured prior to the application of energy from external control unit 52, then both temperature sensors 40, 42 are touching first tissue 20.

Figure 7:
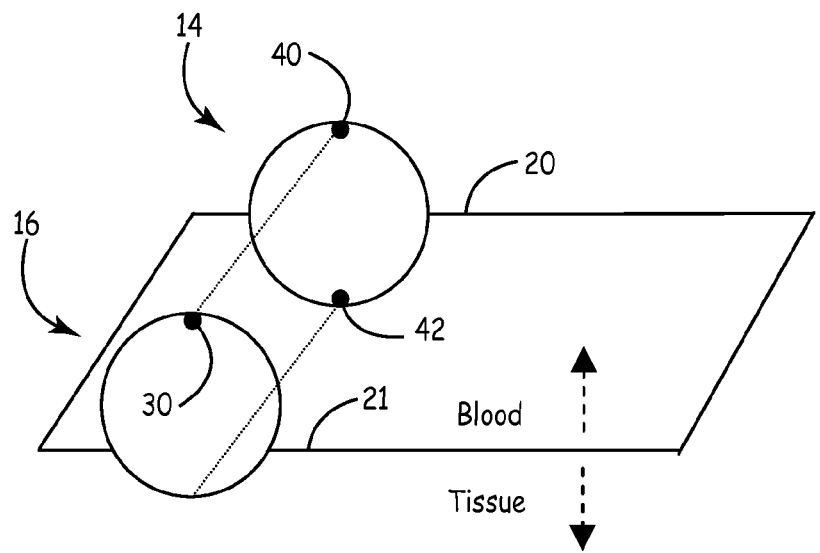
FIG. 7 is a conceptual diagram of a first tissue, a second tissue and two electrodes. One electrode has two temperature sensors. The other electrode has one temperature sensor.

FIG. 7 illustrates electrode 14 with first and second temperature sensors 40, 42 and electrode 16 with third temperature sensor 30. Electrode 14 is proximal to first tissue 20. Electrode 16 is proximal to second tissue 21. As tissue is a poor thermal conductor, the temperature at first tissue 20 and second tissue 21 may differ during the application of power to the tissue through the electrodes. Thus, while first and second temperature sensors 40, 42 are sufficient to determine an orientation of electrode 14 and, thus, infer an orientation of electrode 16, third temperature sensor 30 is used to determine the temperature of second tissue 21 and to regulate the power applied to second tissue 21.

Figure 8:
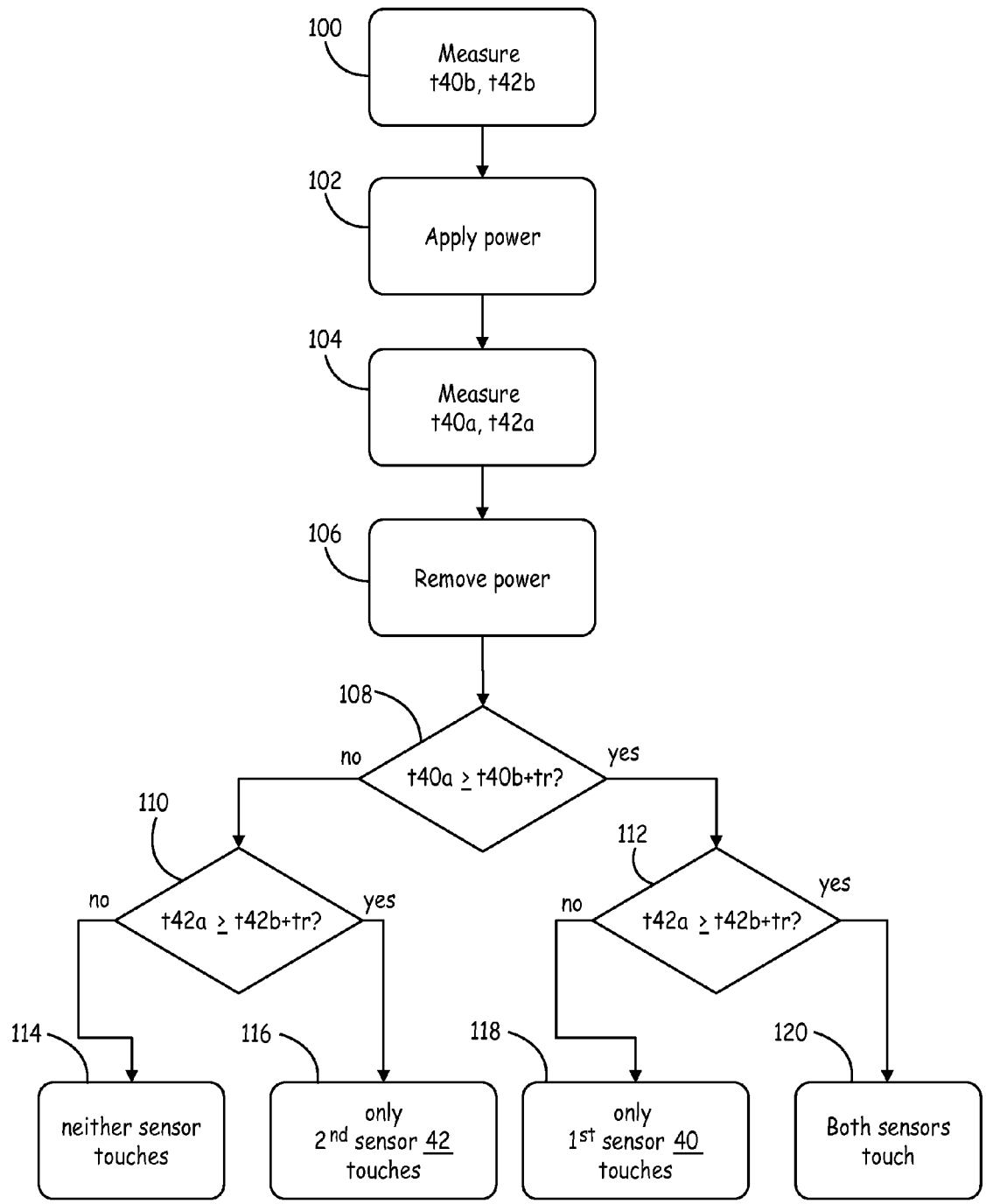
FIG. 8 is a flow diagram of a process to classify the orientation of a catheter.

FIG. 8 is a flow chart showing a method to determine the orientation of catheter 10 via electrode 14. While first and second temperature sensors 40, 42 are within electrode 14 and are not directly exposed to the blood or first tissue 20, references in this application to touching tissue or not touching tissue refer to whether temperature sensors 40, 42 are located in a portion of electrode 14 which is touching or covered by first tissue 20. "Touching tissue", therefore, refers to a temperature sensor being located in a portion of electrode 14 whose corresponding outer portion is touching first tissue 20. "Not touching tissue" has a complementary meaning; that is, "not touching tissue" means the temperature sensor is located in a portion of electrode 14 whose corresponding outer portion is not touching first tissue 20.

In step 100, external control unit 52 measures the temperature of first and second temperature sensors 40, 42. Temperature t40b is the temperature of first temperature sensor 40 before power is applied to first tissue 20 through electrode 14; temperature t42b is the temperature of second temperature sensor 42 before power is applied to first tissue 20 through electrode 14. Proceeding to step 102, power is applied to first tissue 20 through electrode 14. Proceeding to step 104, external control unit 52 measures the temperature of first and second temperature sensors 40, 42. Temperature t40a is the temperature of first temperature sensor 40 after power is applied; temperature t42a is the temperature of second temperature sensor 42 after power is applied. Proceeding to step 106 the external control unit 52 removes the power from electrode 14. Proceeding to step 108, external control unit 52 determines whether there has been a temperature rise that would indicate first temperature sensor 40 is in contact with first tissue 20. A constant, tr, nominally 5 degrees Celsius, is used for this assessment. The constant, tr, may be adjusted depending on the amount of power applied, the type of material, the size, the shape and the thickness of electrode 14. If t40a is greater than or equal to t40b plus tr, indicated "yes" in step 108, FIG. 8, first temperature sensor 40 is determined to be in contact with first tissue 20 and the process proceeds to step 112; if the result is "no", first temperature sensor 40 is determined not to be in contact with first tissue 20 and the process proceeds to step 110.

In step 112, the external control unit 52 determines whether there has been a temperature rise that would indicate second temperature sensor 42 is in contact with first tissue 20. If t42a is greater than or equal to t42b plus tr, indicated "yes" in step 112, FIG. 6, second temperature sensor 42 is determined to be in contact with first tissue 20 and the process terminates in step 120 with the determination that both first temperature sensor 40 and second temperature sensor 42 touch first tissue 20; if the result is "no", second temperature sensor 42 is determined not to be in contact with first tissue 20 and the process terminates in step 118 with the determination that only temperature first sensor 40 touches first tissue 20.

From step 108, if the result is "no", the process proceeds to step 110 where the external control unit 52 determines whether there has been a temperature rise that would indicate temperature sensor 42 is in contact with first tissue 20. If t42a is greater than or equal to t42b plus tr, indicated "yes" in step 110, FIG. 8, second temperature sensor 42 is determined to be in contact with first tissue 20 and the process terminates in step 116 with the determination that second temperature sensor 42 touches first tissue 20; if the result is "no", second temperature sensor 42 is determined not to be in contact with first tissue 20 and the process terminates in step 114 with the determination that neither temperature sensor touches tissue 20.

Figure 9:
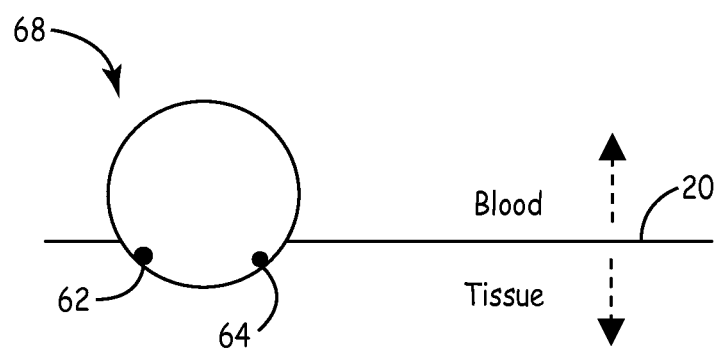
FIG. 9 is a conceptual diagram of a tissue and an electrode with two temperature sensors. The electrode is oriented so both sensors touch the tissue.
Figure 10:
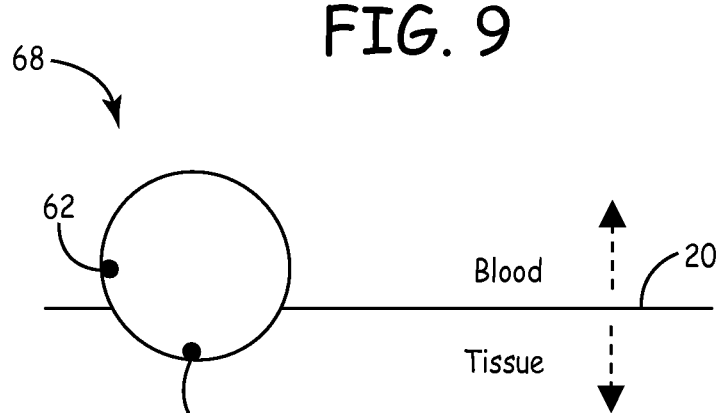
FIG. 10 is a conceptual diagram of a tissue and an electrode with two temperature sensors. The electrode is oriented so one sensor touches the tissue.
Figure 11:
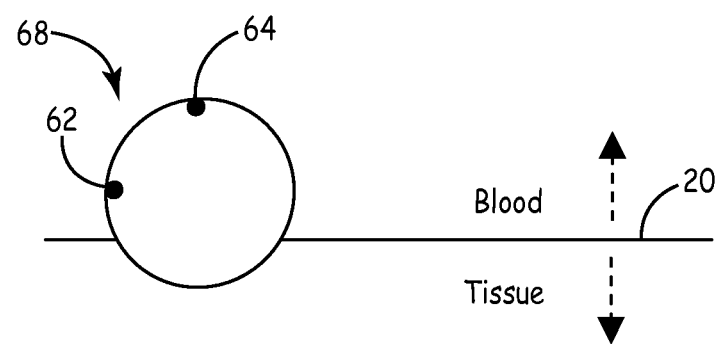
FIG. 11 is a conceptual diagram of a tissue and an electrode with two temperature sensors. The electrode is oriented so neither sensor touches the tissue.

FIGS. 5, 6 depict an embodiment wherein two temperature sensors 40, 42 are disposed in diametric opposition or nearly diametrically disposed in the circumference of electrode 14. FIGS. 9-11 depict an embodiment with electrode 68, wherein, two temperature sensors 62, 64 are disposed in the circumference of electrode 68, however, sensors 62, 64 are not disposed in diametric opposition; rather, they are disposed asymmetrically. Such asymmetric placement of temperature sensors 62, 64 on catheter 68 coupled with external control unit 52 may guide a user to orient catheter 68 so both temperature sensors 62, 64 are in contact with first tissue 20. This has utility for catheter designs with asymmetric apparatus such as with a mechanism or electrode that does not encompass the entire circumference of the catheter but for which direct contact with first tissue 20 or direct contact with the blood is desired. Temperature sensors 62, 64 may correspond to first temperature sensor 40 and second temperature sensor 42 of FIGS. 3-7 and need not be disposed in diametric opposition. While two temperature sensors per electrode are exemplary displayed in FIGS. 3, 5, 6, 9, 10, 11, more than two sensors may be disposed in the circumference of an electrode and coupled to external control unit 52. External control unit 52 may select from a plurality of temperature sensors in the circumference of an electrode and execute the process diagrammed in FIG. 8 to provide an indication to a user of the orientation of catheter 10 relative to first tissue 20 or the blood.

Figure 12:
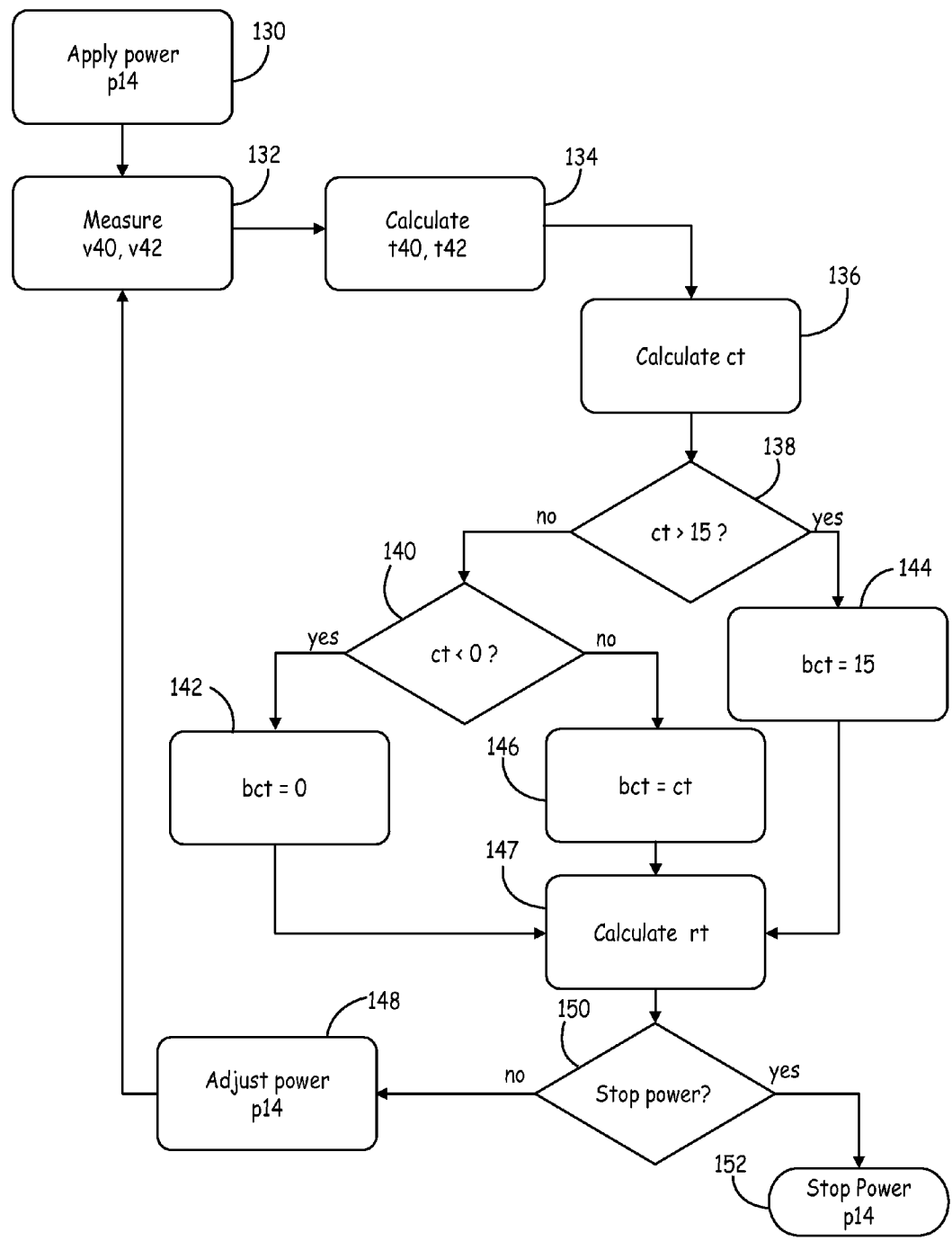
FIG. 12 is a flow diagram of a process to regulate the power applied to a tissue.

With reference to FIG. 12, a user directs external control unit 52 as to a desired duration in seconds and a target temperature for the application of a power to first tissue 20. FIG. 12 is a flow diagram of a method to regulate power p14 applied to first tissue 20 through electrode 14 of catheter 10 based on the voltages received from first and second temperature sensors 40, 42 by external control unit 52. Catheter 10 may have any orientation with respect to first tissue 20 such that first and second temperature sensors 40, 42 may each be in contact with first tissue 20, neither may be in contact with first tissue 20 or one may be in contact with first tissue 20. In step 130, external control unit 52 applies power p14 to first tissue 20 via electrode 14 of catheter 10. Proceeding to step 132, external control unit 52 receives and measures voltage, v40, from first temperature sensor 40 via sensor wires 44, 46; external control unit 52 also receives and measures voltage v42 from second temperature sensor 42 via sensor wires 48, 50. Proceeding to step 134, external control unit 52 calculates temperatures t40, t42 based respectively on measured voltages v40, v42. These calculations are based on prior characterization of first and second temperature sensors 40, 42 which may be implemented as thermocouples. Proceeding to step 136, external control unit 52 calculates compensation temperature, ct, where ct=pc×p+tdc×td+c, pc is a power constant, p is the applied power (see step 130) measured in watts; tdc is a temperature delta constant, td is the absolute difference of temperatures t40 and t42 (see step 134) measured in degrees Celsius and c is a constant. Constants pc, tdc and c may be selected depending on the type of material and the size, the thickness and the shape of electrode 14. Investigations were carried out regarding the heating of electrodes of known orientation with respect to the tissue. Temperatures were measured at multiple positions around the inside circumference of various electrodes leading to an empiric determination of the appropriate constants for use in the equation used to determine the compensation temperature. Where electrode 14 is a platinum band electrode of 2 mm length, pc is 0.21, tdc is 0.46 and c is 4.88; where electrode 14 is a platinum tip electrode of 4 mm length, pc is 0.13, tdc is 0.52 and c is 4.85.

In step 138, external control unit 52 determines whether the calculated value, ct, is greater than 15. If ct is greater than 15 ("yes"), the process continues to step 144 where the bounded compensation temperature, bct, is set equal to 15 and the process continues to step 147. If ct is not greater than 15 ("no"), the process continues to step 140. In step 140, external control unit 52 determines whether ct, is less than 0. If ct is less than 0 ("yes"), bct is set equal to 0 and the process continues in step 147. If ct is not less than 0 ("no"), bct is set equal to ct and the process continues in step 146. In step 147, external control unit 52 calculates a regulation temperature, rt, where rt=bct+tmax and tmax is the maximum of first and second sensor temperatures t40, t42.

In step 150, external control unit 52 determines whether to terminate the application of power to the first tissue 20 through electrode 14 if the desired duration has elapsed from the initial application of power in step 130. If "yes", the process continues to step 152 where the application of power is terminated; if "no", the process continues to step 148 where power p14 applied to tissue 20 through electrode 14 of catheter 10 is adjusted based on a comparison of the target temperature to the regulation temperature. A proportional-integral-derivative controller (PID) controller adjusts power p14 and the process returns to step 132. The process loop starting in step 132 as described above, including adjustment of power p14 (step 148) takes place approximately once per second. In this manner, the process adjusts the applied power to regulate the first tissue 20 temperature to the user directed target temperature based on first and second temperature sensors 40, 42.

Figure 13:
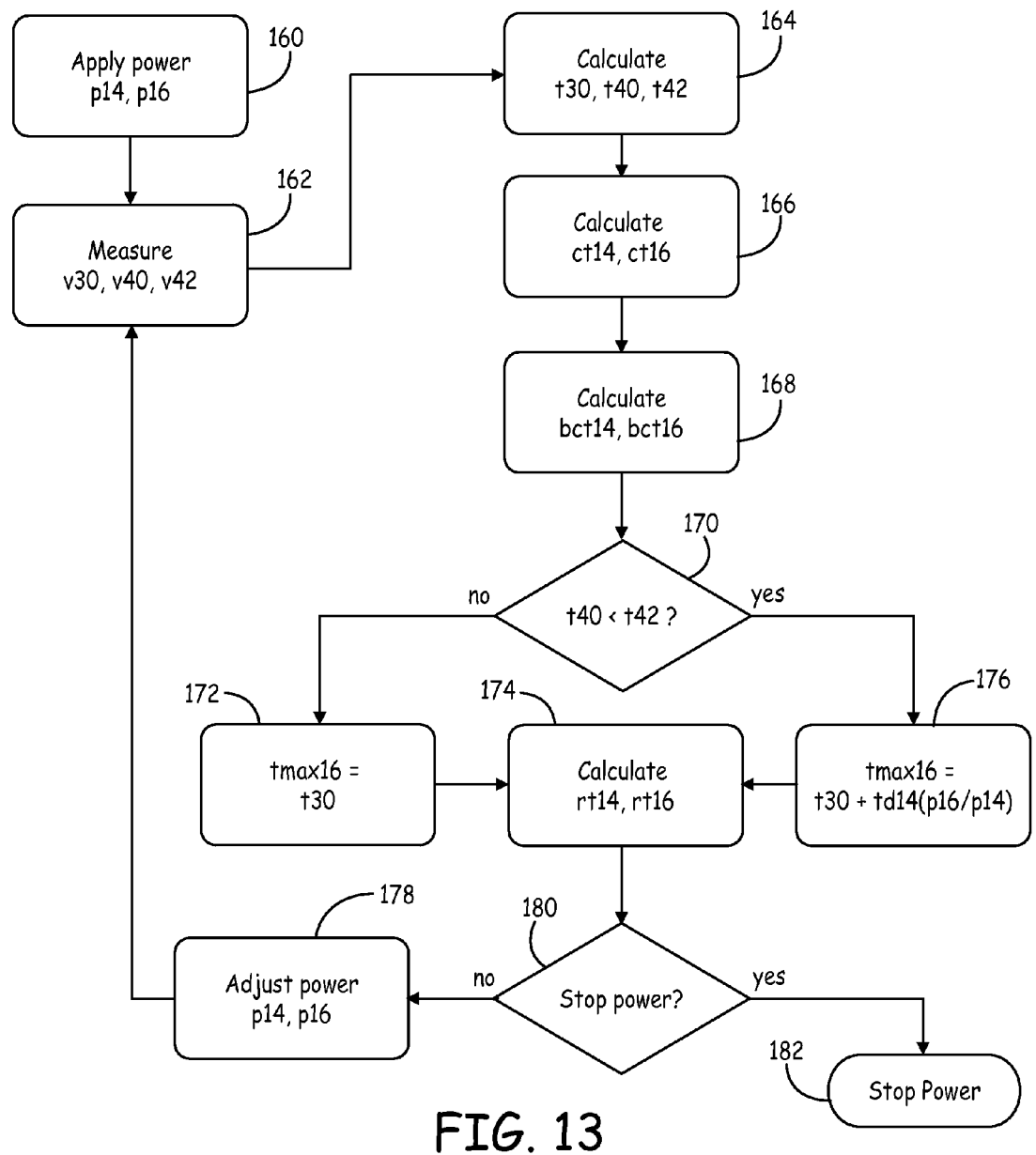
FIG. 13 is a flow diagram of a process to regulate the power applied to two tissues.

With reference to FIGS. 4, 7, FIG. 13 is a flow diagram of a process to regulate power p14 applied to first tissue 20 via electrode 14 based on the voltages received from first and second temperature sensors 40, 42 by external control unit 52 and to regulate power p16 applied to second tissue 21 via electrode 16 based on the voltages received from first, second and third temperature sensors 40, 42, 30. With reference to FIG. 13, a user directs external control unit 52 as to a desired duration in seconds and a target temperature for the application of a power to first tissue 20 and second tissue 21. In this embodiment, catheter 10 is manufactured such that electrodes 30, 40 are in longitudinal alignment (described above). Electrodes 30, 40 both touch a tissue or neither are touching a tissue. Many of the steps illustrated in FIG. 13 correspond to the steps illustrated in FIG. 12 and described above.

In step 160, power p14 is applied to electrode 14 and power p16 is applied to electrode 16. The two power, p14, p16 need not be identical. Continuing, in step 162, external control unit 52 measures voltages v30, v40, v42 from temperature sensors 30, 40, 42, respectively. Continuing in step 164, external control unit 52 translates voltages v30, v40, v42 to temperatures t30, t40, t42, respectively. Continuing in step 166, external control unit 52 calculates compensation temperatures ct14, ct16 for electrodes 14, 16, respectively. As described above for step 136 (FIG. 12), external control unit 52 calculates compensation temperature, ct, where ct14=pc×p14+tdc×td14+c, pc is a power constant, p14 is the applied power to electrode 14 measured in watts; tdc is a temperature delta constant, td is the absolute difference of temperatures t40 and t42 measured in degrees Celsius and c is a constant, calculated in a same manner corresponding to step 136. For electrode 16, only one temperature is available and that is from temperature sensor 30.

The calculation of a compensation temperature requires the difference of temperatures between two temperature sensors. External control unit 52 relies upon temperature measurements from nearby electrode 14 and accommodates for a difference in power applied to each electrode. Temperature rise in an electrode as used for ablation is linearly related to the applied power to each electrode. To calculate compensation temperature ct16, the temperature difference from electrode 14, td14, is scaled by the ratio of power applied to electrodes 14, 16, powers p14, p16, respectively. Temperature difference td16 for electrode 16 is calculated as td16=td14*(p16/p14). Compensation temperature is calculated as ct16=pc×p16+tdc×td16+c, where pc, tdc and c are as described above.

Continuing in step 168, bounded compensation temperatures, bct14, bct16 are calculated in a manner corresponding to steps 138-146 of FIG. 12 and described above. In step 168, the values of compensation temperatures ct14, ct16 are bounded to not be greater than 15 and not less than zero. Continuing, step 170 determines whether electrode 40, which is longitudinally aligned with electrode 30, is the warmer or cooler of temperature sensors 40, 42. If temperature sensor 40 is warmer than temperature sensor 42, then temperature sensor 40 is measuring the temperature of first tissue 20 and sensor 30 is measuring the temperature of second tissue 21. If temperature sensor 40 is not warmer than temperature sensor 42, then temperature sensor 40 is located at a portion of electrode 14 which is bathed in the blood as is temperature sensor 30. If temperature sensor 30 is measuring the temperature of second tissue 21, that is, temperature t40 is not less than temperature 42, external control unit 52 calculates a regulation temperature based on temperature t40 as illustrated in step 172 where tmax16 is set equal to t30. If, however, temperature sensor 30 is measuring at a location that is bathed in the blood rather than the temperature of second tissue 21, a temperature of tissue 21 is estimated as tmax16=t30+td14(p16/p14). The single temperature measured in electrode 16, t30, is augmented in a manner similar that that described above for calculating compensation temperature ct16. Temperature difference, t14, from electrode 14 is multiplied by the ratio of the applied powers, p14, p16, where p14, p16 are the applied powers to electrodes 14, 16, respectively.

Continuing in step 174, regulation temperatures rt14, rt16 are calculated by external control unit 52 where rt14=bct14+tmax14 and tmax14 is the maximum of first and second sensor temperatures t40, t42; rt16=bct16+tmax16; the process for determining tmax16 is described above.

Continuing in step 180, a determination is made as to whether to terminate the application of power to the first tissue 20 through electrode 14 and second tissue 21 through electrode 16, if the desired duration has elapsed from the initial application of power in step 160. If "yes", the process continues to step 182 where the application of power is terminated; if "no", the process continues to step 178 where power p14 applied to first tissue 20 through electrode 14 of catheter 10 and power p16 applied to second tissue 21 through electrode 16, also of catheter 10 are adjusted based on a comparison of the target temperatures to the regulation temperature. A proportional-integral-derivative controller (PID) controller adjusts powers p14, p16 and the process returns to step 162. The process loop starting in step 162 as described above, including adjustment of powers p14, p16 takes place approximately once per second. In this manner, the process adjusts the applied powers p14, p16 to regulate first tissue 20 and second tissue temperatures to the user directed target temperature based on first, second and third temperature sensors 30, 40, 42.

Figure 14:
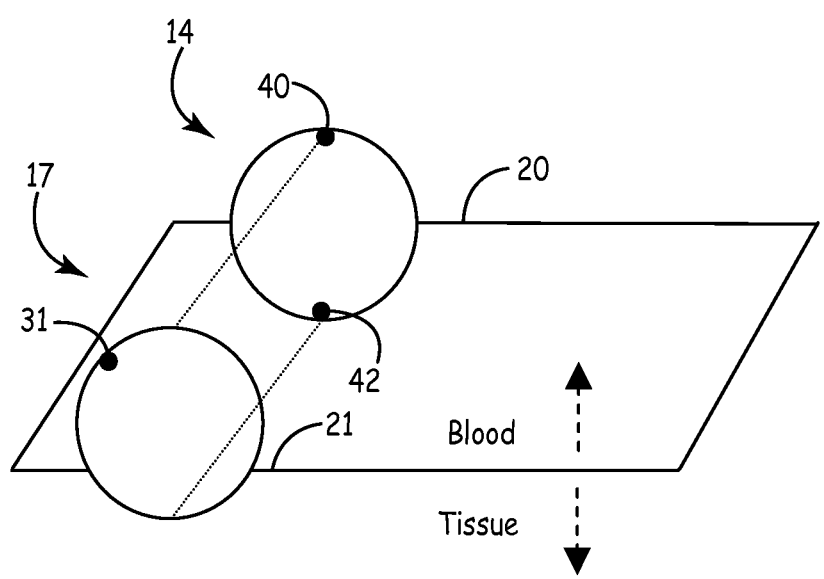
FIG. 14 is a flow diagram of a process to regulate the power applied to two tissues.
Figure 15:
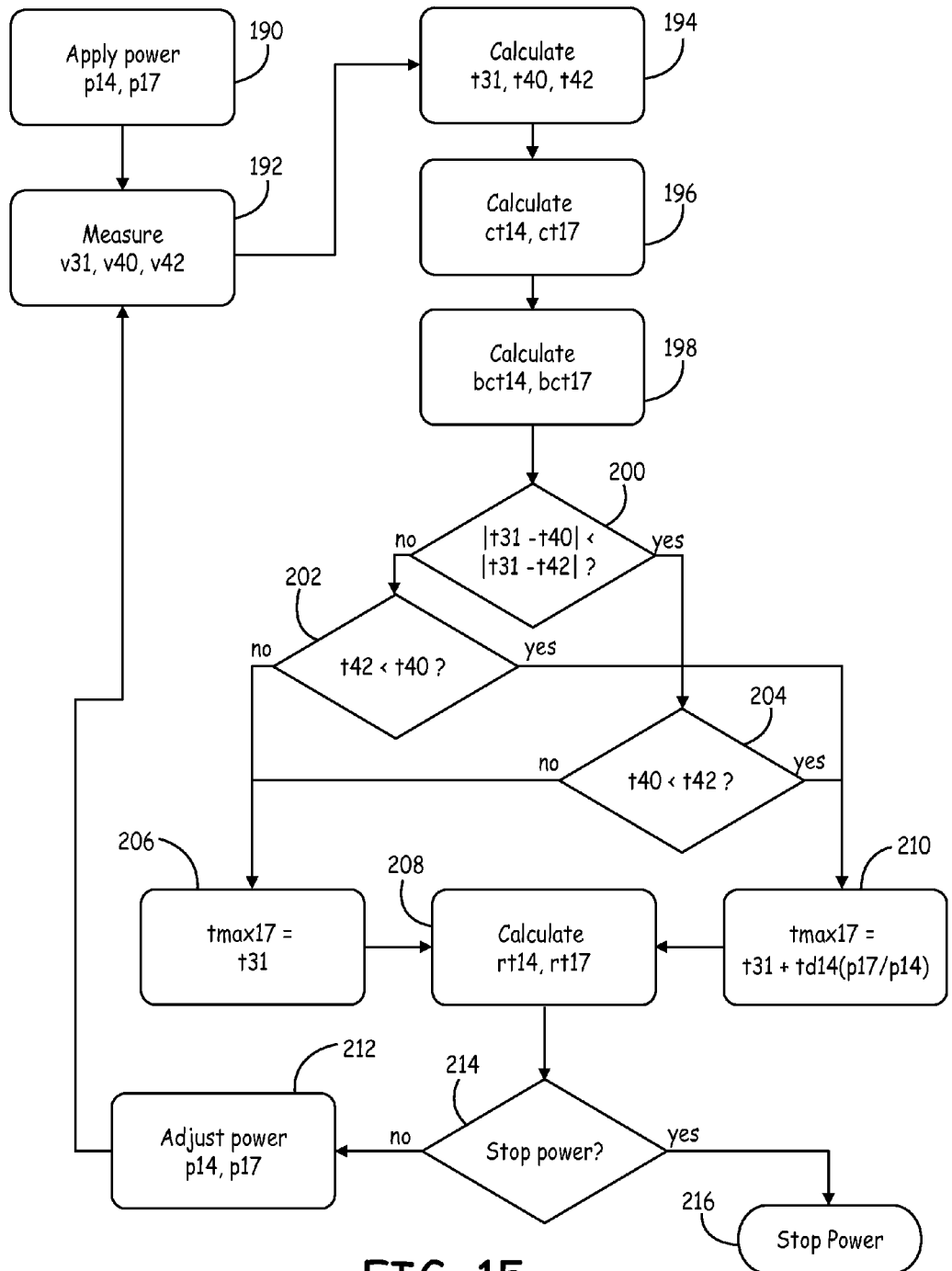
FIG. 15 is a flow diagram of a process to regulate power applied to tissue based on the voltage received from first and second temperature sensors.

With reference to FIG. 14, an embodiment is illustrated that has electrode 14 with first and second temperature sensors 40, 42; nearby electrode 17 has single temperature sensor 31 located on the inside of electrode 17. Unlike the examples illustrated in FIGS. 4, 7, single temperature sensor 31 is not longitudinally aligned with either temperature sensor 40, 42. FIG. 15 illustrates a process to regulate power p14 applied to first tissue 20 via electrode 14 based on the voltages received from first and second temperature sensors 40, 42 by external control unit 52 and to regulate power p16 applied to second tissue 21 via electrode 17 based on the voltages received from first, second and single temperature sensors 40, 42, 31.

With reference to FIG. 15, a user directs external control unit 52 (FIGS. 3, 4) as to a desired duration in seconds and a target temperature for the application of a power to first and second tissues 20, 21. In this embodiment, electrode 31 is not necessarily in longitudinal alignment with electrodes 40, 42 (described above). In step 190, power p14 is applied to electrode 14 and power p17 is applied to electrode 17. The two powers p14, p17 need not be identical. Continuing, in step 192 external control unit 52 measures voltages v31, v40, v42 from temperature sensors 31, 40, 42, respectively. Continuing in step 194, external control unit 52 translates voltages v31, v40, v42 to temperatures t31, t40, t42, respectively. Continuing in step 196, external control unit 52 calculates compensation temperatures ct14, ct17 for electrodes 14, 17, respectively. External control unit 52 calculates compensation temperature, ct14, where ct14=pc×p14+tdc×td14+c, pc is a power constant, p14 is the applied power to electrode 14 measured in watts; tdc is a temperature delta constant, td is the absolute difference of temperatures t40 and t42 measured in degrees Celsius and c is a constant, calculated in a manner corresponding to step 136. For electrode 17, only one temperature is available and that is from temperature sensor 31.

The calculation of a compensation temperature requires the difference of temperatures between two temperature sensors. External control unit 52 relies upon temperature measurements from nearby electrode 14 and when regulating to a temperature, accommodates for a difference in power applied to each electrode. Temperature rise in an electrode as used for ablation is linearly related to the applied power to each electrode. To calculate compensation temperature ct17, the temperature difference from electrode 14, td14, is scaled by the ratio of power applied to electrodes 14, 17, powers p14, p17, respectively. Temperature difference td17 for electrode 17 is calculated as td17=td14*(p17/p14). Compensation temperature is calculated as ct17=pc×p17+tdc×td17+c, where pc, tdc and c are as described above.

Continuing in step 198, bounded compensation temperatures, bct14, bct17 are calculated in a manner corresponding to steps 138-146 of FIG. 12 and described above. In step 198, the values of compensation temperatures ct14, ct17 are bounded to not be greater than 15 and not less than zero. Continuing, step 200 determines which temperature sensor 40, 42 is closer in temperature to t31, that of electrode 31. In step 200, a test is made whether the absolute value of t31-t40 is less than the absolute value of t31-t42. If t31 is closer to t40, the result will be "yes" and the next step is 204. If t31 is not closer to t40 as compared to t42, the result will be "no" and the next step is 202. Step 202 tests whether t40 is warmer than t42. If yes, t40 is warmer, the next step is step 210. If no, t40 is not warmer than t40, the next step is step 206. Step 204 tests whether t42 is warmer than t40. If yes, t42 is warmer, the next step is step 210. If no, t42 is not warmer, the next step is step 206.

In step 206, t31 is closer in temperature to the warmer of the two sensors 40, 42 in electrode 14 and t31 is treated as reflecting the temperature of second tissue 21, tmax17 is set equal to t31. The next step is step 208.

In step 210, t31 is closer in temperature to the cooler of the two sensors 40, 42 in electrode 14 and t31 is treated as reflecting the temperature of an electrode bathed in blood. Temperature tmax is set equal to t31 plus temperature difference td14 (from electrode 14) multiplied by the ratio of powers p17, p14. The next step is 208.

In step 208, regulation temperatures rt14, rt17 are calculated by external control unit 52 where rt14=bct14+tmax14 and tmax14 is the maximum of first and second sensor temperatures t40, t42; rt17=bct17+tmax17 (described above).

Continuing in step 214, a determination is made as to whether to terminate the application of power to the first tissue 20 through electrode 14 and second tissue 21 through electrode 17, if the desired duration has elapsed from the initial application of power in step 190. If "yes", the process continues to step 216 where the application of power is terminated; if "no", the process continues to step 212 where power p14 applied to first tissue 20 through electrode 14 10 and power p16 applied to second tissue 21 through electrode 17 are adjusted based on a comparison of the target temperatures to the regulation temperature. A proportional-integral-derivative controller (PID) controller adjusts powers p14, p17 and the process returns to step 192 The process loop starting in step 192 as described above, including adjustment of powers p14, p17 takes place approximately once per second. In this manner, the process adjusts the applied powers p14, p17 to regulate first tissue 20 and second tissue temperatures to the user directed target temperature based on first, second and single temperature sensors 31, 40, 42.

The invention claimed is:

1. A method to determine a tissue temperature comprising:
   disposing a first thermocouple and a second thermocouple in a catheter, spaced circumferentially apart;
   coupling an external control unit to the thermocouples and to the catheter;
   measuring the thermocouple voltages with the external control unit;
   generating a first power with the external control unit;
   applying the first power through the catheter to a first tissue proximal to the thermocouples;
   calculating the first tissue temperature based on the thermocouple voltages;
   calculating a difference of the thermocouple voltages;
   generating a compensation temperature based on the power and the difference of the voltages;
   calculating a temperature for each voltage;
   calculating a difference of the temperatures; and
   generating a compensation temperature, ct, based on the power and the difference of the temperatures, the compensation temperature being calculated from the equation:

$$ct = pc \times p + tdc \times td + c$$

wherein pc is a power constant, p is the power measured in watts; tdc is a temperature delta constant, td is the absolute difference of the temperatures measured in degrees Celsius and c is a constant.

2. The method of claim 1, further comprising the external control unit classifying a catheter orientation as one of:
   neither thermocouple is touching a tissue,
   only one thermocouple is touching the tissue, and
   both thermocouples are touching the tissue,
   based on the thermocouple voltages.

3. The method of claim 2, further comprising:
   if one thermocouple is touching the tissue, identifying which thermocouple is touching based on the thermocouple voltages.

4. The method of claim 3, further comprising:
   calculating each thermocouple temperature based on each thermocouple voltage;
   and, if only one thermocouple is touching the tissue, identifying the thermocouple which is touching the tissue as the thermocouple with the higher temperature.

5. The method of claim 1, further comprising:
   calculating a bounded compensation temperature, bct, from the equation:

$$bct=0 \text{ for } ct<0; \; bct=ct \text{ for } 0<ct<15; \text{ and } bct=15 \text{ for } ct>15.$$

6. The method of claim 5, further comprising:
   calculating a temperature based on each voltage;
   calculating a tmax, the maximum of the temperatures;
   calculating a regulation temperature, rt, from the equation:

$$rt = bct + tmax$$

and, regulating the power applied to the tissue based on the regulation temperature.

7. The method of claim 6, wherein, $$pc=0.21, \; tdc=0.46, \text{ and } c=4.88$$

or, $$pc=0.13, \; tdc=0.52, \text{ and } c=4.85.$$

8. The method of claim 1, further comprising:
   disposing a third thermocouple in the catheter, spaced longitudinally from the first thermocouple;
   coupling the external control unit to the third thermocouple;
   generating a second power with the external control unit;
   applying the second power through the catheter to a second tissue proximal to the third thermocouple; and
   calculating a second tissue temperature based on the thermocouple voltages.

9. The method of claim 1, further comprising:
   disposing a third thermocouple in the catheter, spaced longitudinally from the first thermocouple;
   coupling the external control unit to the third thermocouple;

generating a second power with the external control unit;
applying the second power through the catheter to a second tissue proximal to the third thermocouple; and
the external control unit classifying a catheter orientation as one of:
  none of the thermocouples is touching a tissue,
  the first and third thermocouples are touching a tissue,
  all three thermocouples are touching a tissue,
based on the thermocouple voltages.

10. The method of claim 9, further comprising regulating the power to the second tissue based on whether the third thermocouple is touching the second tissue.

11. The method of claim 8, further comprising:
calculating a temperature for each of the three thermocouple voltages;
comparing the temperature of the third thermocouple with the temperatures of the first and second thermocouples; and
regulating the power to the second tissue based on the third thermocouple temperature and the first or second thermocouple temperature, whichever is closer in temperature to the third thermocouple temperature.

* * * * *